(12) United States Patent
Nelson

(10) Patent No.: US 7,157,444 B2
(45) Date of Patent: Jan. 2, 2007

(54) AMINOSALICYLATE DERIVATIVES FOR TREATMENT OF INFLAMMATORY BOWEL DISEASE

(76) Inventor: Deanna Jean Nelson, 104 Tasman Ct., Cary, NC (US) 27513

( * ) Notice: Subject to any disclaimer, the term of this patent is extended or adjusted under 35 U.S.C. 154(b) by 240 days.

(21) Appl. No.: 10/688,585

(22) Filed: Oct. 18, 2003

(65) Prior Publication Data

US 2004/0121967 A1    Jun. 24, 2004

Related U.S. Application Data

(60) Provisional application No. 60/435,964, filed on Dec. 21, 2002.

(51) Int. Cl.
| | |
|---|---|
| A61K 31/715 | (2006.01) |
| C07H 5/04 | (2006.01) |
| C07H 5/06 | (2006.01) |
| C07H 1/00 | (2006.01) |
| C08B 37/08 | (2006.01) |

(52) U.S. Cl. .......................... 514/54; 514/53; 514/55; 536/18.7; 536/20; 536/55.2; 536/55.3; 536/124; 252/182.27

(58) Field of Classification Search ............... 536/18.7, 536/20, 55.2, 55.3, 124; 514/53, 54, 55; 252/182.27
See application file for complete search history.

(56) References Cited

OTHER PUBLICATIONS

Tjoernelund et al, Journal of Chromatography, "Stability of 5-Aminosalicylic Acid and its Metabolites in Plasma at −° C: Formation of N-β-D-Glucopyranosyl-5-Aminosalicylic Acid", 1991, vol. 570, No. 1, pp. 224-228.*

Tjoernelund et al reference, Xenobiotica, "New Metabolites of the Drug 5-Aminosalicylic Acid I: N-β-D-Glucopyranosyl-5-Aminosalicylic Acid", 1989, vol. 19, No. 8, pp. 891-899.*

* cited by examiner

Primary Examiner—Shaojia Anna Jiang
Assistant Examiner—Everett White
(74) Attorney, Agent, or Firm—Deanna J. Nelson; Kent Barta

(57) ABSTRACT

Therapeutic 5-aminosalicylic acid derivative compositions having general formula (I), wherein R is a 1-deoxy sugar residue or a poly(ethylene glycol) chain-containing residue, are provided. The compositions enable topical delivery of 5-aminosalicylic acid to the gastrointestinal tract following oral administration in pharmaceutical preparations. According to the invention, the compositions stabilize pharmaceutical compositions containing therapeutic 5-aminosalicylic acid derivatives in a manner that enhances the retention of said compositions in the intestine, decreases the cellular absorption thereof, and decreases the transfer of said compositions or the 5-aminosalicylic acid derived therefrom to the systemic circulation

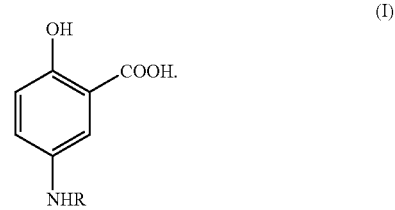

(I)

16 Claims, No Drawings

AMINOSALICYLATE DERIVATIVES FOR TREATMENT OF INFLAMMATORY BOWEL DISEASE

CROSS-REFERENCE TO RELATED APPLICATIONS

Applicant requests benefit of copending provisional patent application 60/435,964, filed Dec. 21, 2002.

STATEMENT REGARDING FEDERALLY SPONSORED RESEARCH & DEVELOPMENT

No Federally sponsored research and development were used in making this invention.

BACKGROUND OF THE INVENTION

Inflammatory bowel disease (IBD) encompasses a spectrum of chronic, idiopathic inflammatory disorders of the gastrointestinal (GI) tract. Disease onset occurs most frequently in early adult life, thus requiring disease management over a lifetime. In the United States alone, over one million people have ulcerative colitis and Crohn's disease, the principal manifestations of IBD. Similar incidences of IBD-related disorders have been reported in the developed countries around the world.

Medical science has not yet discovered a cause or cure for IBD. Aminosalicylates (i.e., 5-aminosalicylic acid and azine compounds structurally related to it) continue to be the initial treatment of choice for both ulcerative colitis and Crohn's disease and are often prescribed to induce or maintain remission as IBD advances in severity. Multi-gram doses of 5-aminosalicylic acid (ASA) and related azine prodrugs, including sulfasalazine, azodisalicylate, and salicylazobenzoic acid, are, in fact, used daily by over half of IBD patients.

Aminosalicylates are topical anti-inflammatory agents. The limited data that are available suggest that the anti-inflammatory effects exhibited by ASA preparations are typical of those observed for phenols. In other words, ASA can act as a reducing agent for oxidants (such as hydroxyl radical, hypohalous acids, and peroxynitrite) and for peroxide intermediates such as the endoperoxides that are formed from arachidonic acid by the action of cyclooxygenase or lipoxygenase. Sandoval et at., for example, have recently reported that ASA is a potent scavenger of peroxynitrite and attenuated peroxynitrite-induced apoptosis in a human intestinal epithelial cell line. [A. Sandoval, et al., *Gastroenterology* 113, 1480–1488 (1997)] Likewise, ASA appears to be a potent scavenger of oxygen- and nitrogen-derived free radicals, which are produced in greater numbers in patients with IBD. (In contrast, N-acetyl-ASA, the principal metabolite of ASA, does not show this activity.) As a salicylate, ASA would be expected to be a metal chelator. Compelling evidence for a protective effect by metal chelation, however, has not been presented. In addition, a number of reports suggest inhibitory activities of ASA that are not related to its ability to undergo oxidation or chelate metals. For example, ASA can inhibit both cyclooxygenase and lipoxygenase, although its potency in this regard is low and apparently concentration dependent.

Despite widespread prescriptive use, neither ASA nor any of its current prodrug forms appears to be an effective treatment for disease of the distal ileum, one of the most common sites for initial IBD onset or relapse. Based on an understanding of the mechanisms of therapeutic action, a substantial basis for this relative lack of therapeutic benefit of oral ASA for patients with advancing IBD can be ascribed to the inability, using available drugs and delivery methods, to deliver therapeutically effective doses of ASA topically to the ileum and to the ileum and colon. Among the ASA drug delivery problems that have not been adequately addressed by current ASA drugs and dosage forms are:

Significant (25–95%) ASA absorption in the proximal ileum following oral administration.

Intracellular uptake and enzymatic conversion to N-acetyl-ASA, an inactive metabolite.

ASA transfer from the GI tract to the systemic circulation, where salicylates are known to inhibit platelet aggregation and exhibit kidney toxicity.

By way of illustration, most unmodified ASA dosage forms (i.e., suspensions, uncoated tablets or capsules containing uncoated ASA) apparently fail to deliver drug to the distal ileum and colon. For example, Yu et al. studied the pharmacological profile of an ASA oral suspension in healthy subjects who had fasted prior to dosage. [D. K. Yu, et al., *J. Clin. Pharmacol* 48, 273–277 (1995)] They found that following ingestion of 40 mL of a suspension of 1 g of ASA in water, there was rapid intestinal uptake of the drug. Within an hour post-dose, the maximum plasma concentrations of the drug and its N-acetylated metabolite N-acetyl-ASA (14.7 and 11.4 µg/mL, respectively) were observed. Within 12 hours the plasma concentrations of these salicylates had decreased to near baseline values. Moreover, less than 1% of the dose was isolated from feces. Since the primary sites of drug uptake are located in the proximal ileum, both observations suggest that little drug reached the distal ileum and colon, the disease sites for most CD patients.

Current techniques for targeting ASA to the ileum and colon comprise solid formulations of the drug molecules that are coated with a pH-sensitive polymeric coating. For example, enteric-release tablet dosage forms of ASA consist of drug particles that are coated with methyl or ethyl cellulose and/or tablets that are coated with a polymer that disintegrates and releases drug at pH 6 and higher. Enteric coating formulations are known which can be used to deliver drugs to the distal ileum, including shellac, acrylic acid derivatives, ethyl cellulose, and cellulose acetate phthalate. [Levine et al., *Gastroenterology* 92: 1037–1044 (1987)]

Drug delivery by enteric-release tablet dosage forms of ASA is better than that of uncoated ASA but continues to present several significant problems. For example, a number of reports confirm that a large and variable percentage of the drug is absorbed in the proximal ileum, decreasing by an unknown and potentially widely variable magnitude the concentration of ASA present at sites of inflammation. [See, for example, M. DeVos, et al., *Gut* 33, 1338–1342 (1992); L. A. Christensen, et al., *Aliment. Pharmacol. Therap.* 4, 523–533 (1990).] As a result of absorption, relatively high concentrations of ASA circulate systemically, potentially presenting salicylate-related safety issues for the patient (e.g., interference with platelet aggregation and kidney damage). A substantial percentage of the drug is converted enzymatically to N-acetyl-ASA, an inactive metabolite.

Azines are a class of ASA-prodrugs traditionally used in the treatment of IBD. Each azine comprises ASA linked to a second molecule by an azo (—N═N—) bond. The azine resists both chemical and enzymatic degradation in the small intestine. The covalently bound ASA that is incorporated in the azine is carried to the colon, where bacterial enzymes reduce the azo bond, thereby releasing the anti-inflammatory ASA at the target site. [U. Klotz, *Clin. Pharmacokin.* 10: 285 (1985)]

While an azine is useful for ASA-delivery to the colon, insufficient 5-aminosalicylic acid is released in the ileum to provide beneficial pharmacological action. Further, the second molecule that is linked to ASA generally has clinical side effects that are undesirable. For example, Khan has reported that the sulfapyridine moiety of the azine sulfasalazine is responsible for many of the undesirable side effects of the azine drug, including nausea, headache, rash, hemolytic anemia, decreased fertility and hepatic toxicity. [A. K. Azad Khan, et al., *Lancet* 2, 892–895 (1977)] In addition, it is reasonable to anticipate that the composition of colonic flora will differ from patient to patient, introducing a potentially variable ability to reduce the azo bond and release ASA in the colon. For these and other reasons, the azines do not address the need for ASA delivery to the distal ileum or the distal ileum and colon.

Several investigational approaches for ASA delivery have also been reported. A modified method to deliver ASA to the colon was reported by Brown, Parkinson, and co-workers who, in order to eliminate the effects of the sulfapyridine fraction, azo-linked sulfasalazine to a high molecular weight polymeric backbone. [J. P. Brown, et al., *J. Med. Chem.* 26: 1300 (1983)] The resulting water-soluble polymer was shown to release ASA in the presence of anaerobic rat cecal bacteria. Pharmacodynamic analysis showed that the polymer also decreased the carrageenan-induced, ulcerative colitis-like inflammatory response in guinea pigs, based on quantitative histopathological results. This pharmacodynamic response was found to be equal to the one achieved after direct administration of ASA and superior to sulfasalazine.

The covalent functionality of aza-aromatic compounds, susceptible to cleavage by the colonic bacteria, was also utilized by Saffran and co-workers. [M. Saffran, et al., *J. Pharm. Sci.* 77: 33 (1988)] It was postulated that a solid dosage form coated with copolymers of styrene and hydroxyethyl methacrylate cross-linked with divinylazobenzene is able to protect the entrapped drug against the digestive enzymes of the stomach and upper portion of the small intestine, and that the polymer is degraded upon arrival at the colon. Indeed, when incubated in fecal content of rat or human for eight days, perforation of the polymer coat was detected microscopically. In addition, sustained pharmacological response to the encapsulated drug was observed when the coated delivery systems were orally administered to rats, and later to dogs. [M. Saffran, et al., *Diabetes* 38S: 81A (1989)]

A colonic delivery system for delivering a drug to the colon is disclosed in U.S. Pat. No. 5,525,634 and U.S. Pat. No. 5,866,619. The system comprises a drug in combination with a saccharide-containing polymer matrix. According to the invention, the matrix is resistant to chemical and enzymatic degradation in the stomach and small intestine. The matrix is degraded in the colon by bacterial enzymatic action, and the drug is released. The system is useful for targeting drugs to the colon in order to treat colonic disease. The system is also useful for enteric administration of drugs that are otherwise absorbed or degraded in the stomach and small intestine.

All of these investigational approaches, however, provide for drug delivery only to the colon. Delivery of therapeutic doses of ASA to the ileum or to the ileum and colon is not achieved.

There exists a need, therefore, for improved ASA prodrugs that can be used to deliver therapeutically effective doses of ASA topically to the ileum and to the ileum and colon following oral administration in pharmaceutical compositions.

SUMMARY OF THE INVENTION

The present invention relates to novel, therapeutic 5-aminosalicylic acid derivative compositions having general formula (I), as well as to a novel method of delivery of 5-aminosalicylic acid to the gastrointestinal tract following oral administration of said 5-aminosalicylic acid derivative compositions in pharmaceutical preparations and to pharmaceutical compositions containing therapeutic 5-aminosalicylic acid derivative compositions having the general formula:

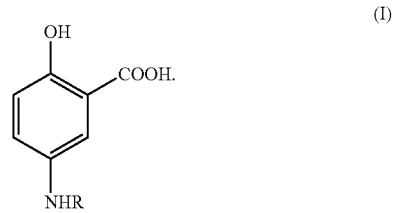

wherein R is a sugar residue or a poly(ethylene glycol)-containing residue.

A first aspect of the present invention is to provide therapeutic 5-aminosalicylic acid derivative compositions having the general formula (I), wherein R is a 1-deoxy sugar residue.

Another aspect of the present invention is to provide therapeutic 5-aminosalicylic acid derivative compositions having the general formula (I), wherein R is a poly(ethylene glycol) chain having the general formula —$CH_2$—($CH_2CH_2O)_n$—$R_1$, $R_1$ is H or a linear or branched lower alkyl group having from one to about 6 carbons, and n is a positive integer from one to about 100.

Yet another aspect of the present invention is to provide therapeutic 5-aminosalicylic acid derivative compositions having the general formula (I), where R is a poly(ethylene glycol) chain having the general formula —$CH_2$—($CH_2CH_2O)_n$—($CH_2)_m$-Z, n is a positive integer from one to about 100, m is 2, 3, or 4, and Z is a pharmacologically active moiety having a molecular weight that is less than about 1000 Daltons that is covalently joined to the distal terminus of said poly(ethylene glycol) chain by a linker group L that is selected from the group consisting of carboxylic acid esters and amides, carbamates, phosphate esters, phosphinate esters, and sulfate esters and amides.

Another object of the present invention is to provide a novel method of topical delivery of 5-aminosalicylic acid to the gastrointestinal tract.

It is a further object of the present invention to provide pharmaceutical compositions containing therapeutic 5-aminosalicylic acid derivative compositions having the general formula (I).

It is also an object of the present invention to stabilize pharmaceutical compositions containing therapeutic 5-aminosalicylic acid derivative compositions having the general formula (I) in a manner that will enhance the retention of said compositions in the intestine, decrease the cellular absorption thereof, and decrease the transfer of said compositions or the 5-aminosalicylic acid derived therefrom to the systemic circulation.

The invention is based upon the recognition that the topical delivery of therapeutically effective amounts of therapeutic 5-aminosalicylic acid derivative compositions having the general formula (I) to the gastrointestinal tract following oral administration in a pharmaceutically acceptable dosage form would enable significant advances in the medical arts, particularly in the treatment of inflammatory bowel diseases.

DETAILED DESCRIPTION OF THE INVENTION

In the description that follows, a number of terms are extensively utilized. In order to provide a clear and consistent understanding of the specification and claims, and the scope to be given such terms, the following definitions are provided.

By the term "drug" is meant any pharmaceutical or physiological agent, composition, bioactive compound, or combination thereof, useful in the diagnosis, cure, mitigation, treatment, or prevention of a disease, or for any other medical or veterinary purpose. The term "drug" is intended to be interpreted broadly and is not limited in terms of chemical composition or biological activity.

By the term "therapeutic agent" is meant an agent which is therapeutically useful, e.g., an agent for the prevention, treatment, remission or attenuation of a disease state, physiological condition, symptoms, or etiological factors, or for the evaluation or diagnosis thereof.

By the term "poly(ethylene glycol) chain" is meant a polymeric chain of atoms having the general formula —$(CH_2CH_2O)_n$— where n is a positive integer having a value greater than about 3. If n has a value of about 3 to about 20, the term "oligo(ethylene glycol) chain" is an equivalent descriptor. Poly(ethylene glycol) itself is a diol having the general formula HO—$(CH_2CH_2O)_n$—H, and monomethylpoly(ethylene glycol) (MPEG), a widely used family of poly(ethylene glycol) derivatives, has the general formula HO—$(CH_2CH_2O)_n$—$CH_3$. The hydroxyl group of both poly(ethylene glycol) and MPEG is readily converted using conventional chemistries to a halogen, an amino group, or an ester of a carboxylic, carbamic, phosphoric, phosphonic, sulfuric or sulfonic acid.

The present invention is based on the recognition that the therapeutic need for a therapeutic 5-aminosalicylic acid derivative composition having a significantly better therapeutic benefit:risk ratio can be addressed by modifying 5-aminosalicylic acid to reduce ASA transfer across biological membranes of the intestinal lumen and to maintain its physiological and pharmacological activity as an anti-inflammatory agent.

Persons skilled in the pharmaceutical arts use the "rule of 5" to predict when poor absorption or permeation of the gut by a drug is likely to be observed. [C. Lipinski, *Amer. Pharm. Rev.* 5(3), 82–85 (2002)] This mnemonic predicts that a drug will exhibit poor oral bioavailability (in other words, low uptake from the GI tract and transfer to the systemic circulation following ingestion) when (1) there are more than 5 H-bond donors; (2) the molecular weight (size) of the molecule is over 500 Daltons; (3) the log P [where P is the water (buffer):octanol distribution ratio] is over 5; and (4) the sum of nitrogen and oxygen atoms in the molecule is over 10.

Before the discovery leading to the invention disclosed herein, it was not recognized that structural modification of ASA to meet the conditions of the "rule of 5" is useful for reducing ASA transfer across biological membranes of the intestinal lumen, for maintaining therapeutic concentrations of an ASA-derivative composition in the intestinal lumen, and for maintaining its pharmacological activity as an anti-inflammatory agent. Thus, for the first time, the present invention discloses that conjugating the amino group of 5-ASA to a second molecule ("R") accomplishes these objectives, provided that the second molecule "R" is a sugar (as in embodiment 2A) or that "R" consists of a poly (ethylene glycol) (PEG) chain covalently joined to the nitrogen atom in the amino group of ASA at its proximal terminus and covalently joined to hydrogen, an alkyl group, or a drug at its distal terminus. In embodiments of the present invention, the distal PEG-terminus can be either an inert "anchor" (e.g., as is the methyl group in MPEG, as in embodiment 2B) or a drug (e.g., an immunomodulator, antibacterial, or antioxidant, or other pharmacologically active agent as in embodiment 2C).

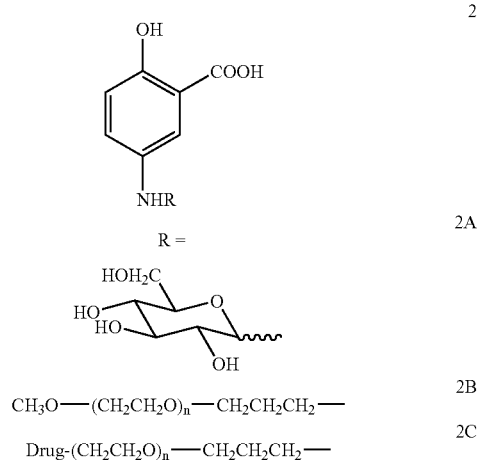

Thus, in one embodiment of the present invention, R is a sugar residue in which a covalent bond to the oxygen of a hydroxyl group originally substituted on the parent sugar compound has been replaced by a covalent bond to the nitrogen of the amino group substituent on ASA. In a preferred embodiment of the present invention, R is a 1-deoxydisaccharide residue. In a more preferred embodiment of the present invention, R is a 1-deoxymono-saccharide residue. In a most preferred embodiment of the present invention, R is a 1-deoxy-D-glucosyl or 1-deoxy-D-galactosyl residue.

Compounds in accordance with this embodiment of the present invention are readily prepared by reaction of the carbonyl group of the desired sugar with the amino group of 5-aminosalicylic acid. This method of preparation is described by Nelson and Lavin [*J. Carbohyd. Chem.* 4(1): 91–97 (1985)]. In order to undergo this reaction, the sugar must be a reducing sugar. A monosaccharide, disaccharide, or polysaccharide that meets this criterion is suitable. In one preferred embodiment of the present invention, the reducing sugar is a disaccharide, including maltobiose, lactobiose, cellobiose, and N,N-diacetylchitobiose. In a more preferred embodiment of the present invention, the reducing sugar is a monosaccharide, including fucose, fructose, N-acetylglucosamine, and N-acetylgalactosamine. In a most preferred embodiment of the present invention, the reducing sugar is glucose or galactose.

Alternatively, compounds in accordance with this embodiment of the present invention are readily prepared by reaction of a 1-amino-1-deoxyglycosylamine with a 1- to 2-fold excess of 5-aminosalicylic acid in the presence of a tertiary amine (e.g., triethylamine or pyridine) and an organic solvent, such as dimethylsulfoxide, dimethylformamide, pyridine, and 2,6-lutidine. Methods for the preparation of N-linked glycoconjugates are disclosed in U.S. Pat. No. 5,668,272.

Another aspect of the present invention is to provide therapeutic 5-aminosalicylic acid derivative compositions having the general formula (I), wherein R is a poly(ethylene glycol) chain having the general formula —$CH_2CH_2CH_2$—($CH_2CH_2O$)$_n$—$R_1$, $R_1$ is H or a linear or branched lower alkyl group having from one to about 6 carbons, and n is a positive integer from about 3 to about 100.

Compounds in accordance with this embodiment of the present invention are readily prepared by reaction of the aldehyde group of the desired poly(ethylene glycol) aldehyde or dialdehyde [in other words, HC(O)—($CH_2CH_2O$)$_n$—H or HC(O)—($CH_2CH_2O$)$_n$—$CH_2CH_2C(O)H$, respectively] or monoalkylated poly(ethylene glycol)-ω-aldehyde [i.e., $R_1O$—$CH_2CH_2O$)$_n$—$CH_2CH_2$—C(O)H, where $R_1$ and n are as described above] with 5-aminosalicylic acid and subsequent reduction of the imine intermediate that is formed thereby using a reducing agent such as sodium cyanoborohydride, sodium borohydride, borane-trimethylamine, or tri(2-carboxyethyl)phosphine (TCEP). Methods for the reductive amination of poly(ethylene glycol) aldehydes have been described by Guillaumie et al. [F. Guillaumie, et al., *Bioconj. Chem.* 13, 285–295 (2002)]

Yet another aspect of the present invention is to provide therapeutic 5-aminosalicylic acid derivative compositions having the general formula (I), where R is a poly(ethylene glycol) chain-containing tether having the general formula —$CH_2CH_2CH_2$—($CH_2CH_2O$)$_n$—($CH_2$)$_m$-Z, n is a positive integer from about 3 to about 100, m is 2, 3, or 4, the proximal terminus of said poly(ethylene glycol) chain is covalently joined to the nitrogen atom in the amino group of 5-aminosalicylic acid, and Z is a pharmacologically active moiety having a molecular weight that is less than about 1000 Daltons that is covalently joined to the distal terminus of said poly(ethylene glycol) chain by a linker group L that is selected from the group consisting of carboxylic acid esters and amides, carbamates, phosphate esters, phosphonate esters, and sulfate and sulfonate esters and amides.

Compounds in accordance with this embodiment of the present invention are readily prepared in two steps, excluding protection/deprotection steps that can be necessitated by the presence of reactive groups on the drug molecule that will interfere with the desired covalent bond formation to ASA. In a first step, the aldehyde group of an ω-hydroxy- or a protected ω-amino-poly(ethylene glycol)-α-aldehyde is allowed to react with 5-aminosalicylic acid to form an imine intermediate, and then the imine intermediate produced therefrom is reduced to a secondary amine using a reducing agent such as sodium cyanoborohydride, sodium borohydride, borane-trimethylamine, or TCEP. In this manner, an ω-hydroxy- or a protected ω-amino-poly(ethylene glycol) chain is covalently joined to the nitrogen atom of the amino group of 5-aminosalicylic acid. If a protective group is present, it is removed using conventional chemistries. In a second step, N-(ω-hydroxy- or ω-amino-poly(ethylene glycol))-ASA is allowed to react with a suitably activated carboxylic, carbamic, phosphoric, phosphonic, sulfuric or sulfonic acid moiety that is a structural component of a drug or that can be used as a linker group L to covalently join a hydroxyl or amino substituent on a drug to the ω-hydroxy- or ω-amino group on the poly(ethylene glycol) chain. The synthetic steps can be re-ordered to enable obtaining the desired product in higher yield, purity, with greater safety to manufacturing personnel, and so forth.

ASA potentially has three sites that are suitable for covalent modification: the carboxyl group, the adjacent phenolic hydroxyl group, and the amine group. In the novel prodrugs that comprise the present invention, neither the phenolic hydroxyl nor the carboxyl group has been modified, since modification of one group, but not the other, would leave the modified site open to more facile hydrolysis. Similarly, modification of both groups would eliminate any metal chelating ability of the prodrug, an unrecognized but potentially important mechanism of therapeutic action. In contrast, alkylation of the amino group has been selected as the optimal site for structural modification of ASA, since current ASA prodrugs that are based on modification at this site (the azines, for example) have been found to be orally active.

Acylation of an amino group is a common strategy that is used to modify the pharmacological properties of a drug. In fact, fatty acids are frequently used for this purpose. However, fatty acid acylation increases lipophilicity and reduces water solubility, thereby changing the pharmacological properties in ways that are undesirable for purposes of the present invention. Moreover, the fact that N-acetyl-ASA (an acetylated derivative of ASA) is much less therapeutically active for the treatment of IBD than is ASA suggests that acylation will reduce the therapeutic activity of ASA.

In contrast, the inventor believes that alkylation of the amino group of ASA is a much more useful method for obtaining therapeutic ASA derivative compositions that retain topical anti-inflammatory activity. Specifically, if the amino group of ASA is alkylated with sugars or PEG, the aqueous solubility and log P value of the new prodrug composition are increased. Both increased aqueous solubility and higher log P values are properties that correlate with reduced penetration across biological membranes.

Moreover, glycosylation is not expected to adversely affect the safety of the ASA prodrug of the present invention, since glycosylated-ASA has been identified as a metabolite of ASA. [J. Tjornelund, et al., *Xenobiotica* 19, 891–899 (1989)] Likewise, poly(ethylene glycol) (PEG) conjugation has been widely used to alter the pharmacological properties of drugs and biologics. [J. M. Harris and S. Zalipsky, Eds. *Poly(ethylene glycol): Chemistry and Biological Applications*, American Chemical Society, 1997] Structural modification of ASA with either a PEG or MPEG compound offers the further advantages that both PEG and MPEG compounds are commercially available in a range of molecular weights and that PEG chemistries that enable conjugation to the amino group of ASA are well documented.

Alkylation of the amino group of ASA with an aldehyde-substituted PEG segment having a molecular weight in the range of 400–3000 Daltons is useful for the purposes of the present invention and is a most preferred embodiment of the present invention. Higher molecular weight PEGs (MW 3,500 and 5,000) are also useful in the present invention. However, since PEG-diols and MPEG-monoalcohols having molecular weights of 3,500 or 5,000 Daltons are used clinically to induce bowel movements (e.g., GoLytely™, a prescription drug marketed by Schwarz Pharma), their corresponding ASA prodrugs can cause diarrhea, and are, therefore, less preferred embodiments of the present invention. Very high molecular weight PEGs (>5,000 Daltons) can actually promote absorption by membranes of the GI tract, an undesirable outcome, and are least preferred embodiments of the present invention.

Alkylation of the amino group of ASA with PEG also affords opportunities to tether other drugs and therapeutic agents to ASA, thereby providing novel ASA-prodrugs that exhibit the therapeutic benefits of both ASA and the drug covalently joined thereto. Conventional chemistries are useful for covalently joining a halogen, hydroxyl or amino group at the distal terminus of a reductively alkylated ASA derivative composition of the present invention to a carboxylic, carbamic, phosphoric, phosphonic, sulfuric, or sulfonic acid substituent on the second drug that has been suitably activated for reaction. These linker groups have been selected because they are subject to both chemical and enzymatic hydrolysis in vivo, processes that sever the covalent bond between the N-alkylated ASA derivative and the drug tethered thereto. The drug that is tethered to ASA in the manner described in the present invention can be selected from broad spectrum of pharmaceutical and diagnostic agents. Although a disparity is daily dosing requirements ($\geq$2 g ASA daily vs. a few mg//kg/day dose of the second drug) might restrict the choice of drug tethered to ASA in this way, this determination is generally known in the art.

By way of example, one embodiment of a therapeutic ASA derivative composition of the present invention is the moiety in which lipoic acid is covalently joined to ASA via PEG (e.g., where lipoic acid is the "Drug" of general formula 2C). Incorporation of lipoic acid in this embodiment is reasonable, in that the role of lipoic acid in human energy metabolism is well documented. As lipoamide, it functions as a cofactor in the multi-enzyme complexes that catalyze the oxidative decarboxylation of alpha-keto acids including pyruvate. Recently, a great deal of attention has been focused on the antioxidant activities of LA and its reduced form, dihydrolipoic acid (DHLA). It forms a redox couple with DHLA, and the two compounds (LA and DHLA) can act synergistically. Both LA and DHLA exhibit various properties including quenching of reactive oxygen and nitrogen species (e.g., hydroxyl radical, peroxyl radicals, superoxide, hypochlorous acid, and peroxynitrite) and metal chelation ($Cd^{2+}$, $Fe^{3+}$, $Cu^{2+}$, $Zn^{2+}$). They are also capable of interacting with other antioxidants including ascorbate, glutathione, and ubiquinol and are thought to participate in ascorbate recycling and indirectly in the regeneration of alpha-tocopherol. LA is soluble in both lipid and aqueous environments, and is readily absorbed from the diet, transported to cells, and reduced to DHLA. Daily doses of 600 mg of lipoic acid were found to counter the effects of oxidative stress, as measured by the levels of F2-isoprostanes in the urine, plasma protein carbonyls, and susceptibility of low-density lipoprotein to oxidation. [K. Marangon, et al., *Free Radical Biol. Med.* 27(9/10), 1114–1121 (1999)] In further support of this choice, oral supplementation with thiol antioxidants related to lipoic acid has been shown to restore intracellular glutathione levels and attenuate colonic inflammation in an animal model of colitis. [K. P. Pavlick, et al., *Free Radical Biol. Med.* 33(3), 311–322 (2002)]

Another object of the present invention is to provide a novel method of delivery of 5-aminosalicylic acid to the gastrointestinal tract. Site-specific drug delivery offers several benefits over traditional drug therapy. Side effects can be reduced and pharmacological response increased if the active drug can be delivered specifically to its site of action.

Therapeutic ASA derivative compositions of the present invention afford the advantage that their physicochemical characteristics minimize absorption and transfer from the lumen of the intestine to the systemic circulation following oral or topical administration. As a result, if drug concentrations are determined at intralumenal sites along the length of the intestine at various intervals post-administration, drug concentrations in the range from about 20% to about 90% or more of the administered dose is expected, indicating that therapeutically effective amounts of ASA derivative compositions of the present invention are better maintained. In contrast, following oral or topical administration of ASA, from 5% to 95% of the drug might be absorbed in the proximal ileum and transferred to the systemic circulation or enzymatically altered to reduce its therapeutic anti-inflammatory activity. Therapeutic ASA delivery to the distal ileum and colon is severely compromised under these latter conditions.

It is also an object of the present invention to stabilize pharmaceutical compositions containing therapeutic 5-aminosalicylic acid derivative compositions having the general formula (I) in a manner that will enhance the retention of said compositions in the gastrointestinal tract following ingestion and decrease the transfer of said compositions or the 5-aminosalicylic acid derived from said compositions from the lumen of the gastrointestinal tract to the systemic circulation.

The "rule of 5" is a mnemonic widely used by pharmaceutical artisans to predict that a drug will exhibit low uptake from the GI tract and transfer to the systemic circulation following oral ingestion or topical administration. An embodiment of the present invention in which the therapeutic ASA derivative composition of general formula (I) and R is a sugar residue has the following physicochemical characteristics: (1) more than 5H-bond donors; (2) a molecular weight of at least 300 Daltons if the sugar residue is a 1-deoxymonosaccharide and >500 Daltons if the sugar residue is a 1-deoxydisaccharide or 1-deoxypolysaccharide; (3) a log P value of over 1; and (4) a sum of nitrogen and oxygen atoms in the molecule of at least 9. Likewise, an embodiment of the present invention in which the therapeutic ASA derivative composition of general formula (I) in which R is a PEG-containing residue has the following physicochemical characteristics: (1) more than 5H-bond donors; (2) a molecular weight of at least 600 Daltons; (3) a log P value of over 1; and (4) a sum of nitrogen and oxygen atoms in the molecule of at least 9. In general, therefore, the mnemonic predicts that all embodiments of an ASA derivative composition of the present invention will be retained in the lumen of the GI tract, and will have low uptake by cells and tissues of the GI tract and transfer to the systemic circulation as compared to ASA.

The prediction that a therapeutic ASA derivative composition of the present invention will have low uptake from the GI tract and transfer to the systemic circulation as compared to equivalent doses of ASA is validated by oral or topical administration of a therapeutic ASA derivative composition followed by analytical determinations, at time zero and various intervals following administration, of (i) the concentrations of the therapeutic ASA derivative composition and (ii) the ASA released from it at multiple sites within the intestine and in the systemic circulation. Thus, following oral or topical administration, a therapeutically useful ASA derivative composition of the present invention exhibits characteristics such as the following: (1) the retention of high percentages of the administered dose of the therapeutic ASA derivative composition at all sites within the lumen of the intestine or, in the alternative, at all sites post-drug release, if a controlled release dosage form is employed; (2) low chemical or enzymatic conversion to ASA at any one site within the lumen of the intestine; (3) a low concentration of the ASA derivative composition or its metabolites and ASA and its principal metabolite, N-acetyl-ASA, in the systemic circulation; (4) anti-inflammatory activity that parallels or exceeds that exhibited by equivalent doses of ASA administered in the same manner; and (5) general safety, in that the recipient of the administered dose maintains overt well-being for a 24-hour period after receipt of the dose. Thus, a preferred embodiment of a therapeutic ASA derivative composition is expected to exhibit at least about 20% retention of the administered dose within the lumen of the intestine and an anti-inflammatory activity that is at least equal to that of an equivalent dose of ASA.

Pharmaceutical compositions comprising therapeutic 5-aminosalicylic acid derivative compositions as described above are also provided. Whilst it can be possible for a therapeutic agent composition of the present invention to be administered as the raw chemical, it is preferable to present it as a pharmaceutical composition. According to embodiments of the present invention, a pharmaceutical composition includes one or more of the therapeutic 5-aminosalicylic acid derivative compositions described above, and a pharmaceutically acceptable carrier.

The therapeutic composition comprising a physiologically active 5-aminosalicylic acid-containing therapeutic agent having the general formula (I) can be formulated for administration in a pharmaceutical carrier in accordance with known techniques. See, for example, Remington, *The Science and Practice of Pharmacy* (9$^{th}$ Ed. 1995).

In the manufacture of a pharmaceutical composition according to embodiments of the present invention, a 5-aminosalicylic acid-containing therapeutic agent composition is typically admixed with, inter alia, a pharmaceutically acceptable carrier. The carrier must, of course, be acceptable in the sense of being compatible with any other ingredients in the pharmaceutical composition and should not be deleterious to the patient. The carrier can be a solid or a liquid, or both, and is preferably formulated with the 5-aminosalicylic acid-containing therapeutic agent composition as a unit-dose formulation. The pharmaceutical compositions can be prepared by any of the well-known techniques of pharmacy, including, but not limited to, admixing the formulation components, optionally including one or more accessory ingredients.

The pharmaceutical compositions according to embodiments of the present invention include those suitable for oral, rectal, topical, inhalation (e.g., via an aerosol), buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces), intraocular, and transdermal administration. The most suitable route in any given case will depend on the nature and severity of the condition being treated and on the nature of the particular therapeutic 5-aminosalicylic acid derivative composition which is being used.

Pharmaceutical compositions suitable for oral administration are the most preferred embodiments of the present invention and can be presented in discrete units, including capsules, cachets, lozenges, or tablets, each containing a predetermined amount of a therapeutic 5-aminosalicylic acid derivative composition; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the therapeutic 5-aminosalicylic acid derivative composition and a suitable carrier (which can contain one or more accessory ingredients as noted above). In general, the pharmaceutical composition according to embodiments of the present invention are prepared by uniformly and intimately admixing the therapeutic 5-aminosalicylic acid derivative composition with a liquid or finely divided solid carrier, or both, and then, if necessary, shaping the resulting mixture. For example, a tablet can be prepared by compressing or molding a powder or granules containing the therapeutic 5-aminosalicylic acid derivative composition, optionally with one or more accessory ingredients. Compressed tablets can be prepared by compressing, in a suitable machine, the therapeutic 5-aminosalicylic acid derivative composition in a free-flowing form, including a powder or granules optionally mixed with a binder, lubricant, inert diluent, and/or surface active or dispersing agent(s). Molded tablets can be made by molding, in a suitable machine, the powdered compound moistened with an inert liquid binder. The tablets can optionally be coated or scored and can be formulated so as to provide slow or controlled release of the active ingredient therein.

Pharmaceutical compositions suitable for buccal (sub-lingual) administration include lozenges comprising the conjugated therapeutic agent composition in a flavored base, usually sucrose and acacia or tragacanth; and pastilles comprising the conjugated therapeutic agent composition in an inert base including gelatin and glycerin or sucrose and acacia.

Pharmaceutical compositions according to embodiments of the present invention suitable for parenteral administration comprise sterile, aqueous and non-aqueous injection solutions of the conjugated therapeutic agent composition, which preparations are preferably isotonic with the blood of the intended recipient. These preparations can contain antioxidants, buffers, bacteriostats, and solutes which render the composition isotonic with the blood of the intended recipient. Aqueous and non-aqueous sterile suspensions can include suspending agents and thickening agents. The compositions can be presented in unit-dose or multi-dose containers, for example, sealed ampoules and vials, and can be stored in a freeze-dried (lyophilized) condition requiring only the addition of the sterile liquid carrier, for example, saline or water for injection, immediately prior to use. Extemporaneous injection solutions and suspensions can be prepared from sterile powders, granules, and tablets of the kind previously described. For example, an injectable, sterile composition comprising a therapeutic 5-aminosalicylic acid derivative composition in a unit dosage form in a sealed container can be provided.

Pharmaceutical compositions suitable for rectal administration are preferably presented as unit-dose suppositories. These can be prepared by admixing the therapeutic 5-aminosalicylic acid derivative composition with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Pharmaceutical compositions suitable for transdermal administration can be presented as discrete patches adapted to remain in intimate contact with the epidermis of the recipient for a prolonged period of time. Compositions suitable for transdermal administration can also be delivered by iontophoresis [see, for example, *Pharmaceutical Research* 3(6): 318 (1986)] and typically take the form of an optionally buffered aqueous solution of the conjugated therapeutic agent composition. Suitable formulations comprise citrate or bis-tris buffer (pH 6) or ethanol/water and contain from 0.1 to 0.2 M active ingredient.

It should be understood that in addition to the ingredients particularly mentioned above, the formulations of this invention can include other agents conventional in the art having regard to the type of formulation in question; for example, those suitable for oral administration can include flavoring agents.

Preferred unit dosage formulations are those containing an effective dose, as hereinbelow recited, or an appropriate fraction thereof, of the active ingredient.

According to other embodiments of the present invention, methods of treating a patient in need of such treatment include administering to the patient an effective amount of a therapeutic 5-aminosalicylic acid derivative composition comprising a physiologically active therapeutic 5-aminosalicylic acid derivative composition as described above. The therapeutically effective amount of any therapeutic 5-aminosalicylic acid derivative composition, the use of which is in the scope of the present invention, will vary somewhat from one composition to another, and from patient to patient, and can depend on factors such as the age and condition of the patient and the route of delivery. Such dosages can be determined in accordance with routine pharmacological procedures known to those skilled in the art. As a general proposition, a therapeutically effective dose of therapeutic 5-aminosalicylic acid derivative composition will be the weight of active pharmaceutical ingredient per kilogram of the patient's body weight (i.e., mg/kg) that is useful for the prevention, prophylaxis, treatment, remission or attenuation of a disease state, physiological condition, symptoms, or etiological factors, or for the evaluation or diagnosis thereof. The duration of treatment depends on the type of condition being treated and can be for as long as the life of the patient.

The following Examples illustrate the present invention.

EXAMPLE 1

Preparation of 5-(1-deoxy-D-glycosylamino)salicylic acid

At least 1.5 mole equivalent of D-(+)-glucose is allowed to react with 5-aminosalicylic acid in methanol/water solution containing 1.1 mole equivalents of triethylamine. The reaction is monitored by thin-layer chromatography (TLC) (silica gel; eluent: CHCl$_3$:MeOH, 1:1, by volume). The solvent is removed, and the reaction mixture is purified by chromatography on silica gel or BIOGEL-F2™ (BioRad, Richmond, Calif.), using absorbance at 254 nm as detection. The products are characterized by TLC on silica gel, electrospray mass spectrometry, and $^1$H- and $^{13}$C-NMR analysis. The transamination reaction is indicated by a downfield shift of resonance of the anomeric proton (observed at δ=4.1 ppm by analysis of unsubstituted D-glucose) to δ=4.3–4.7 ppm in the $^1$H-NMR spectrum of the β-anomer of the synthetic glycoconjugate product. (This anomer is the major product of the transamination reaction.) This procedure is taken from the report of D. Nelson and M. Lavin, *J. Carbohyd. Chem.* 4(1): 91–97 (1985).

EXAMPLE 2

Preparation of 5-(glycosyl-1'-amino-1'-deoxy)salicylic acid

Beta-D-glucosylamine is prepared by the reaction of D-(+)-glucose with ammonium bicarbonate as described by Likhosherstov, L. M. et al. (*Carbohydr. Res.* 146: C1, 1986). A reaction mixture containing the glycosylamine and a 1- to 2-fold excess by weight of 5-aminosalicylic acid is allowed to react overnight in pyridine at 50° C. The reaction is monitored by thin-layer chromatography (TLC) (silica gel; eluent: CHCl$_3$:MeOH, 1:1, by volume). The solvent is removed, and the reaction mixture is purified by chromatography on silica gel or BIOGEL-F2™ (BioRad, Richmond, Calif.), using absorbance at 254 nm as detection. The products are characterized by TLC on silica gel, electrospray mass spectrometry, and $^1$H- and $^{13}$C-NMR analysis. The transamination reaction is indicated by a downfield shift of resonance of the anomeric proton (observed at δ=4.1 ppm by analysis of the unsubstituted glycosyl-1-amine) to δ=4.3–4.7 ppm in the $^1$H-NMR spectrum of the β-anomer of the synthetic glycoconjugate product. (This anomer is the major product of the transamination reaction.)

EXAMPLE 3

Preparation of Other Glycoconjugates of 5-Aminosalicylic Acid

Glycoconjugates containing 5-aminosalicylic acid are obtained from other 1-amino-1-deoxysugars derived from glucose, mannose, fucose, galactose, cellobiose, maltose, lactose, N,N-diacetylchitobiose, and N-acetyllactosamine, for example, are prepared as described in Examples 1 and 2. Purity of the glycoconjugates is verified by reversed-phase HPLC [SPHERISORB C18 (5 m particle size) column (Alltech, Deerfield, Ill.)] using isocratic delivery of a mobile phase consisting of 20% aqueous acetonitrile. The products are characterized by TLC on silica gel, electrospray mass spectrometry, and $^1$H- and $^{13}$C-NMR analysis. The transamination reaction is indicated by a downfield shift of resonance of the anomeric proton (observed at δ=4.1 ppm by analysis of the unsubstituted glycosyl-1-amine) to δ=4.3–4.7 ppm in the $^1$H-NMR spectrum of the β-anomer of the synthetic glycoconjugate product. (This anomer is the major product of the transamination reaction.)

EXAMPLE 4

Preparation of 5-(MPEG-amino)salicylic acid

MPEG-aldehyde (Mol. Wt. 1000 Daltons; 600 mg, 0.6 mmol) is dissolved in dimethylformamide (DMF) to provide a 0.5 M solution. The resulting solution is then added to a 0.5 M solution of 5-aminosalicylic acid (76.5 mg, 0.5 mmol) in DMF. MP-Triacetoxyborohydride resin (2.3 mmol/g, 0.760 g, 1.75 mmol; Argonaut, Foster City, Calif.) is added, and the resulting slurry is agitated at room temperature for about 16 hours. The MP-resin is filtered with a 6-mL fritted polypropylene cartridge into a scintillation vial containing MP-TsOH (1.0 g, 1.5 mmol; Argonaut, Foster City, Calif.). The MP-triacetoxyborohydride resin is rinsed with DMF (3×2 mL), and the combined filtrate is agitated with MP-TsOH for 45 min. The mixture is transferred to a polypropylene cartridge fitted with a nylon stopcock to control the flow rate to approximately 0.5–1.5 mL/min. The MP-TsOH resin is washed with methanol (4×8 mL) to remove non-basic impurities. The product is released by washing with 2 M $NH_3$/MeOH and MeOH (2×8 mL). The combined solution is concentrated to afford the product. The product is characterized by UV-visible spectroscopy, $^1$H-NMR, and mass spectrometry. The log P value is also obtained.

For larger scale reactions, the use of sodium cyanoborohydride, TCEP, or a solution of trimethylamine borane in tetrahydrofuran as the reducing agent is recommended as a more cost-effective alternative to use of the macroporous resin described above.

EXAMPLE 5

Preparation of Lipoamide-PEG-ASA

α-BOCamido-PEG-ω-aldehyde (Mol. Wt. 1000 Daltons; 600 mg, 0.6 mmol) is dissolved in dimethylformamide (DMF) to provide a 0.5 M solution. The resulting solution is then added to a 0.5 M solution of 5-aminosalicylic acid (76.5 mg, 0.5 mmol) in DMF. MP-Triacetoxyborohydride resin (2.3 mmol/g, 0.760 g, 1.75 mmol; Argonaut, Foster City, Calif.) is added, and the resulting slurry is agitated at room temperature for about 16 hours. The MP-resin is filtered with a 6-mL fritted polypropylene cartridge into a scintillation vial containing MP-TsOH (1.0 g, 1.5 mmol; Argonaut, Foster City, Calif.). The MP-triacetoxy-borohydride resin is rinsed with DMF (3×2 mL), and the combined filtrate is agitated with MP-TsOH for 45 min. The mixture is transferred to a polypropylene cartridge fitted with a nylon stopcock to control the flow rate to approximately 0.5–1.5 mL/min. The MP-TsOH resin is washed with methanol (4×8 mL) to remove non-basic impurities. The product is released by washing with 2 M $NH_3$/MeOH and MeOH (2×8 mL). The combined solution is concentrated to afford the product. The product, N-(α-BOCamido-PEG-$CH_2CH_2CH_2$)-5-aminosalicylic acid (BOCamido-PEG-ASA), is characterized by UV-visible spectroscopy, $^1$H-NMR, and mass spectrometry.

For larger scale reactions, the use of sodium cyanoborohydride, TCEP, or a solution of trimethylamine-borane in tetrahydrofuran as the reducing agent is recommended as a more cost-effective alternative to use of the macroporous resin described above.

In a second step, the BOC-protecting group is removed from the amino group of BOCamido-PEG-ASA by treatment with trifluoroacetic acid. The amino-PEG-ASA derivative thus obtained is allowed to react with 1.1 equivalents of the N-hydroxysuccinimide activated ester of lipoic acid in tetrahydrofuran solution containing triethylamine. The product, lipoamide-PEG-ASA, is isolated and purified by chromatography, and is then characterized by UV-visible spectroscopy, $^1$H-NMR, and mass spectrometry. The log P value is also obtained.

EXAMPLE 6

In Vitro Study of the Anti-Inflammatory Activity of the ASA Prodrugs Using an Endothelial Adhesion Molecule Surface-Expression Assay Surface-expression of P-selectin and ICAM-1 was assayed using the method of Khan et al. [B. V. Khan, et al., *J. Clin. Invest.* 95, 1262–1270 (1995)]. Human umbilical vein endothelial cells (HUVEC) monolayers were grown in 48-well plates, and treated with either 20 ng/ml TNF-α (24 h), or pre-treated with an ASA prodrug of the present invention (or ASA, as a control) and then treated with 20 ng/ml TNF-α (24 h). After treatment, the cells were fixed with 0.25 mL of 1% paraformaldehyde in phosphate buffered saline (PBS) for 10 minutes at room temperature. After washing three times with 1 mL Hank's Balanced Salts Solution (HBSS)/PBS (1:1) solution, monolayers were incubated with an anti-P-selectin antibody (10 μg/mL) or an anti-ICAM-1 antibody (10 μg/mL) in HBSS/PBS+5% fetal calf serum (FCS) at 37° C. for 30 minutes. Monolayers were washed twice with 0.5 mL HBSS/PBS solution, and then incubated with horseradish peroxidase-conjugated goat anti-mouse IgG (1:10,000 diluted, Sigma, St. Louis, Mo.) in HBSS/PBS+5% FCS at 37° C. for 30 minutes. Monolayers were washed four times with 0.5 mL HBSS/PBS followed by incubation with 0.25 mL of 0.003% hydrogen peroxide+ 0.1 mg/mL 3,3', 5,5'-tetramethylbenzidine (Sigma) in acetone at 37° C. for 60 minutes in the dark. The color reaction was stopped by adding 75 μl of 8 N $H_2SO_4$, and the samples were transferred to 96-well plates which were read on a plate reader at 450 nm, blanking on monolayers stained only with a secondary antibody.

All values are expressed as means±SE. Data were analyzed using a one-way ANOVA with Bonferroni corrections for multiple comparisons. Probability (p) values of <0.05 were considered significant.

A useful therapeutic ASA derivative composition of the present invention will exhibit anti-inflammatory activity in this assay that is equal to or greater than that of ASA.

EXAMPLE 7

Effects of Oral Administration of an ASA-Prodrug of the Present Invention in a Rodent Model of Ulcerative Colitis Acid-induced intestinal inflammation in animals is a widely used model of human intestinal inflammation. Effects of the ASA-prodrugs of the present invention will be screened used a rat model of severe colitis.

A. Induction of Colitis. Dextran sulfate sodium (DSS) colitis is induced in test animals by mixing 3% (wt/vol) DSS (mol wt 44 kiloDaltons; source: TdB Consultancy AB, Uppsala, Sweden) into the drinking water (distilled) provided ad libitum. Control (sham-colitis) groups receive distilled water without DSS.

B. Treatment. After induction of colitis or sham-colitis, the animals are observed for three days. Animals in each treatment group receive an ASA derivative composition twice each day as an oral bolus. Animals in the treatment control group receive an equivalent dose of ASA twice each day as an oral bolus. On day 4, study animals are weighed and anesthetized. The descending colon is surgically removed, freed from surrounding tissues, opened, weighed, and processed for histological and immunochemical analyses.

C. Evaluation of Clinical Colitis. In all animals, weight, stool blood, presence of gross blood and daily stool consistency are determined daily. Disease activity index (DAI) is determined by combining scores of a) weight loss, b) stool consistency and c) bleeding (divided by 3). Each score was determined as follows:

change in weight (0–1%, 1; 1–5%, 2; 5–10%, 3; 10–15%, 4; >15%);

stool blood (0: negative; 2: positive; or gross bleeding: 4); and stool consistency (0: normal; 2: loose stools; 4: diarrhea).

D. Histological Analysis. Distal colon samples are fixed in Zamboni's fixative (overnight) and embedded in JB4 (Polysciences). 5 μm thickness sections are stained with hematoxylin/eosin, and scored (blinded) by a GI pathologist. Histological damage is scored using the criteria described by Cooper et al. [H. S. Cooper, et al. Lab. Invest. 69, 238–249 (1993)]. Crypt damage is scored on 0–4 grade [grade 0: intact crypt; grade 1: loss of the basal one-third of the crypt; grade 2: loss of the two-thirds of the crypt; grade 3: loss of entire crypt with the surface epithelium remaining intact; grade 4: loss of the entire crypt and surface epithelium (erosion)]. These changes are also quantified with respect to the percent of area involved in the disease process: (1) 1 to 25%; (2) 26 to 50%; (3) 51 to 75%; (4) 76 to 100%. Crypt damage score is calculated as the sum of the grade of the crypt and percent area score. The inflammation is evaluated subjectively on a 0–3 scale, and the extent of involvement estimated as: (1) 0 to 25%; (2) 26 to 50%; (3) 51 to 75%; (4) 76 to 100% of total surface area. The inflammation score is determined as the sum of the inflammation grade and the percent extent score.

E. Expression of MAdCAM-1. Distal colon samples are held in Zamboni's fixative overnight at +4° C. and then embedded in Tissue-Tek O.C.T Compound (Sakura, Finetek) and frozen at −20° C. 10 μm thickness sections are cut by cryostat. Non-specific staining is blocked by incubating samples in normal donkey serum (10%, Sigma Chemicals, St. Louis) diluted in antibody diluent (Biogenex, San Ramon, Calif.) for 30 min at 25° C. Sections are incubated in 1% antibody (rat anti-MAdCAM-1 [clone MECA 367, Pharmingen, San Diego, Calif.)] (1 h, 25° C.), washed in PBS (3×, 10 min), and incubated in 2% antibody (diluted 1:200) goat anti-rat conjugated to Cy3 (Jackson ImmunoResearch Laboratories, West Grove, Pa.). After tissues are incubated with 2% antibody, they are washed in PBS (3×, 10 min) and mounted in 10 μL Vectashield mounting medium (Vector Laboratories, Burlingame, Calif.) to minimize fluorescent photo-bleaching.

F. Statistical Analysis. Results are expressed as mean±SE. Significant differences are assessed by one-way ANOVA plus Fisher's PLSD test. P values <0.05 will be accepted as statistically significant.

A useful therapeutic ASA derivative composition of the present invention will exhibit anti-inflammatory activity that is equal to or greater than that of an equivalent dose of ASA.

EXAMPLE 8

Determination of the Disposition of ASA-Prodrug in Patients

The biopharmaceutical and clinical pharmacokinetic profile of each ASA prodrug test preparation will be studied in healthy volunteers and in patients. Control groups will receive an equivalent dose of ASA delivered in the same manner. Each test subject will receive a test dose, administered orally, three times daily for a period of fourteen days. Plasma concentrations of the ASA prodrug, ASA and N-acetyl-ASA will be monitored hourly for 8 hours following each dose. Complete urine will be collected during the 0–8 and 8–24 hour periods. In addition, 24-hour feces will be collected. The data will be analyzed to calculate the elimination half-life from the plasma, the mean steady-state plasma levels, and the fraction of each dose that is recovered in the urine and feces.

In a similar study that will be completed in ileostomates, test subjects will be fasted overnight and then ingest a dose of the ASA prodrug test preparation. The ileostomy effluent and urine will be collected for 24 hours post-dosage; plasma samples will be collected prior to dosage and then hourly for six hours and at 8, 12, and 24 hours post-dosage. The data will be used to determine the small bowel transit times; the times at which the ASA prodrug, ASA or N-acetyl-ASA are first detected in the plasma, the maximum plasma concentrations of these salicylates, and the times at which these concentrations peak; and the percentage of the administered dose that is recovered in the urine.

A useful therapeutic ASA derivative composition of the present invention will exhibit small bowel transit times and percentage of the administered dose that is recovered in the urine that are equal to or greater than those of an equivalent dose of ASA; prolonged times at which the ASA prodrug, ASA, or their principal metabolites are first detected in the plasma; and lower maximum plasma concentrations of these salicylates.

With respect to a therapeutic 5-aminosalicylic acid derivative composition of the present invention, the skilled artisan will appreciate that a therapeutic 5-aminosalicylic acid derivative composition exhibits enhanced pharmaceutical and pharmacological properties as compared to the unmodified therapeutic agent, 5-aminosalicylic acid, including, but not restricted to, improved topical bioavailability in the lumen of the intestine, the ability to interact with biological membranes of the intestine with limited uptake and transfer to the systemic circulation, reduced side effects, and enhanced resistance to enzymatic degradation.

The invention has been described with respect to several particular examples and embodiments. However, the foregoing examples and descriptions are not intended to limit the invention to the exemplified embodiments. The skilled artisan should recognize that variations can be made within the scope and spirit of the invention as described in the foregoing specification. The invention encompasses all alternatives, modifications, and equivalents that can be included within the true scope and spirit of the invention as defined by the appended claims.

I claim:

1. A therapeutic 5-aminosalicylic acid derivative composition having the general formula:

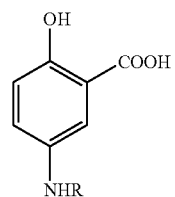

wherein R is a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol) chain-containing residue having the general formula —$CH_2CH_2$—$CH_2$($CH_2CH_2O)_n$—$R_1$, $R_1$, is H or a linear or branched lower alkyl group having from one to about 6 carbons, and n is a positive integer from about 3 to about 100; or a poly (ethylene glycol) chain-containing tether having the general formula —$CH_2$—$(CH_2CH_2O)_n$—$(CH_2)_m$-Z, in which n is a positive integer from about 3 to about 100, m is 2, 3, or 4, and Z is a drug or therapeutic agent having a molecular weight that is less than about 1000 Daltons that is covalently joined to the distal terminus of said poly(ethylene glycol) chain-containing tether.

2. A therapeutic 5-aminosalicylic acid derivative composition having the general formula:

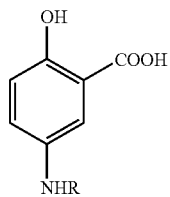

wherein R is a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative.

3. A therapeutic 5-aminosalicylic acid derivative composition having the general formula:

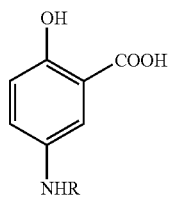

wherein R is a poly(ethylene glycol) chain-containing residue having the general formula —$CH_2$—$(CH_2CH_2O)_n$—$R_1$, $R_1$ is H or a linear or branched lower alkyl group having from one to about 6 carbons, and n is a positive integer from about 3 to about 100.

4. A therapeutic 5-aminosalicylic acid derivative composition having the general formula:

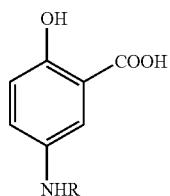

wherein R is a poly(ethylene glycol) chain-containing residue having the general formula —$CH_2$—$(CH_2CH_2O)_n$—$R_1$, $R_1$ is H or a linear or branched lower alkyl group having from one to about 6 carbons, and n is a positive integer from 3 to about 20.

5. A therapeutic 5-aminosalicylic acid derivative composition having the general formula:

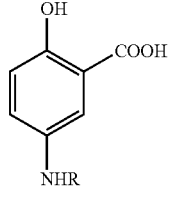

wherein R is a poly(ethylene glycol) chain-containing tether having the general formula —$CH_2$—$(CH_2CH_2O)_n$—$(CH_2)_m$-Z, n is a positive integer from one to about 100, m is 2, 3, or 4, and Z is a drug or therapeutic agent having a molecular weight that is less than about 1000 Daltons that is covalently joined to the distal terminus of said poly(ethylene glycol)-containing tether.

6. A method for preparing a therapeutic 5-aminosalicylic acid derivative composition having the general formula:

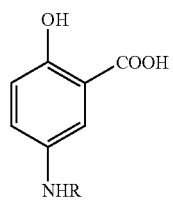

wherein R is a 1-deoxy sugar, comprising reacting the amino group of 5-aminosalicylic acid with a reducing sugar in an aqueous alcohol solution.

7. A method for preparing a therapeutic 5-aminosalicylic acid derivative composition having the general formula:

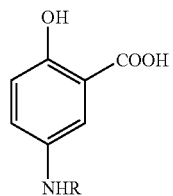

wherein R is a poly(ethylene glycol) chain-containing residue having the general formula —$CH_2CH_2CH_2$—$(CH_2CH_2O)_n$—$R_1$, $R_1$ is H or a linear or branched lower alkyl group having from one to about 6 carbons, and n is a positive integer from about 3 to about 100, comprising alkylating the amino group of 5-aminosalicylic acid with a poly(ethylene glycol) chain-containing aldehyde or halide.

8. A method of preparing a therapeutic 5-aminosalicylic acid derivative composition having the general formula:

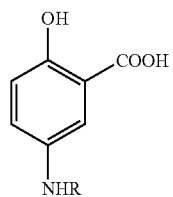

wherein R is a poly(ethylene glycol) chain-containing tether having the general formula —$CH_2$—$(CH_2CH_2O)_n$—$(CH_2)_m$-Z, n is a positive integer from about 3 to about 100, m is 2, 3, or 4, and Z is a drug or therapeutic agent having a molecular weight that is less than about 1000 Daltons that is covalently joined to the distal terminus of said poly (ethylene glycol) chain-containing tether, comprising the following steps:
   a) reacting the amino group of 5-aminosalicylic acid with a poly(ethylene glycol) chain-containing aldehyde or halide to provide a poly(ethylene glycol) chain-containing alkylated amino group of 5-aminosalicylic acid;

b) covalently joining said drug or therapeutic agent Z to the distal terminus of said poly(ethylene glycol) chain-containing alkylated amino group of 5-aminosalicylic acid.

9. A pharmaceutical composition suitable for administration to a subject in need thereof comprising a physiologically active therapeutic agent composition and a pharmaceutical carrier, wherein said therapeutic agent composition comprises a physiologically active 5-aminosalicylic acid derivative composition having the general formula:

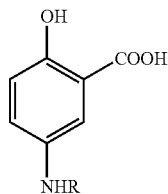

wherein R is a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol) chain-containing residue having the general formula $-CH_2CH_2CH_2-(CH_2CH_2O)_n-R_1$, $R_1$ is H or a linear or branched lower alkyl group having from one to about 6 carbons, and n is a positive integer from about 3 to about 100; or a poly(ethylene glycol) chain-containing tether having the general formula $-CH_2-(CH_2CH_2O)_n-(CH_2)_m$-Z, in which n is a positive integer from about 3 to about 100, m is 2, 3, or 4, and Z is a drug or therapeutic agent having a molecular weight that is less than about 1000 Daltons that is covalently joined to the distal terminus of said poly(ethylene glycol) chain-containing tether.

10. A method of prophylactically or interventionally treating an inflammatory disease in the gastrointestinal tract of a human or non-human mammalian subject, comprising administering to the subject an effective amount of a therapeutic 5-aminosalicylic acid derivative composition having the general formula:

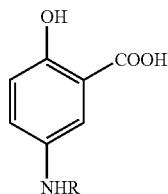

wherein R is a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol) chain-containing residue having the general formula $-CH_2CH_2CH_2-(CH_2CH_2O)_n-R_1$, $R_1$ is H or a linear or branched lower alkyl group having from one to about 6 carbons, and n is a positive integer from about 3 to about 100; or a poly(ethylene glycol) chain-containing tether having the general formula $-CH_2-(CH_2CH_2O)_n-(CH_2)_m$-Z, in which n is a positive integer from about 3 to about 100, m is 2, 3, or 4, and Z is a drug or therapeutic agent having a molecular weight that is less than about 1000 Daltons that is covalently joined to the distal terminus of said poly(ethylene glycol) chain-containing tether.

11. A method of prophylactically or interventionally delivering 5-aminosalicylic acid to the gastrointestinal tract of a subject comprising administering to the subject a pharmaceutical formulation comprising an effective amount of a therapeutic 5-aminosalicylic acid derivative composition having the general formula:

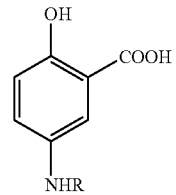

wherein R is a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol) chain-containing residue having the general formula $-CH_2CH_2CH_2-(CH_2CH_2O)_n-R_1$, $R_1$ is H or a linear or branched lower alkyl group having from one to about 6 carbons, and n is a positive integer from about 3 to about 100; or a poly(ethylene glycol) chain-containing tether having the general formula $-CH_2-(CH_2CH_2O)_n-(CH_2)_m$-Z, in which n is a positive integer from about 3 to about 100, m is 2, 3, or 4, and Z is a drug or therapeutic agent that is selected from the group consisting of lipoic acid, immunomodulators, antibacterials, and antioxidants, wherein the drug or therapeutic agent is covalently joined to the distal terminus of said poly(ethylene glycol) chain-containing tether; and a pharmaceutical carrier.

12. A method of stabilizingly and structurally modifying 5-aminosalicylic acid in a manner that enhances its retention in the gastrointestinal tract and decreases the transfer of said acid from the lumen of the gastrointestinal tract to the systemic circulation of a subject comprising covalently conjugating the nitrogen atom of the amino group of 5-aminosalicylic acid to a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol)-containing residue having the general formula $-CH_2CH_2CH_2-(CH_2CH_2O)_n-R_1$, wherein $R_1$ is H or a linear or branched lower alkyl group having from one to about 6 carbons, and n is a positive integer from about 3 to about 100; or a poly(ethylene glycol) chain-containing tether having the general formula —CH₂—(CH₂CH₂O)ₙ—(CH₂)ₘ-Z, in which n is a positive integer from about 3 to about 100, m is 2, 3, or 4, and Z is a drug or therapeutic agent that is selected from the group consisting of lipoic acid, immunomodulators, antibacterials, and antioxidants, wherein the drug or therapeutic agent is covalently joined to the distal terminus of said poly(ethylene glycol) chain-containing tether.

13. A physiologically active therapeutic 5-aminosalicylic acid derivative composition having the general formula:

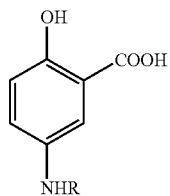

wherein R is a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol) chain-containing residue having the general formula —CH₂CH₂CH₂—(CH₂CH₂O)ₙ—R₁, R₁ is H or a linear or branched lower alkyl group having from one to about 6 carbons, and n is a positive integer from about 3 to about 100; or a poly(ethylene glycol) chain-containing tether having the general formula —CH₂—(CH₂CH₂O)ₙ—(CH₂)ₘ-Z, in which n is a positive integer from about 3 to about 100, m is 2, 3, or 4, and Z is a drug or therapeutic agent that is selected from the group consisting of lipoic acid, immunomodulators, antibacterials, and antioxidants, wherein the drug or therapeutic agent is covalently joined to the distal terminus of said poly(ethylene glycol) chain-containing tether, wherein the derivative composition is active in the prophylaxis or treatment of inflammatory conditions or disease states in a mammalian subject or a cell or tissue from said subject.

14. The composition according to claim 13, wherein the therapeutic 5-aminosalicylic acid derivative composition has an enhanced in vivo resistance to enzymatic degradation, relative to 5-aminosalicylic acid alone.

15. A method of stabilizingly and structurally modifying 5-aminosalicylic acid in a manner that enhances its retention in the gastrointestinal tract and decreases the transfer of said acid from the lumen of the gastrointestinal tract to the systemic circulation of a subject comprising covalently conjugating the nitrogen atom of the amino group of 5-aminosalicylic acid to a reducing sugar that is selected from the group consisting of galactose, fucose, fructose, N-acetylglucosamine, N-acetylgalactosamine, maltobiose, lactobiose, cellobiose, and N,N-diacetylchitobiose, wherein a covalent bond to the oxygen of a hydroxyl group originally substituted on the reducing sugar has been replaced by a covalent bond to the nitrogen of the amino group of the 5-aminosalicylic acid derivative; a poly(ethylene glycol)-containing residue having the general formula —CH₂CH₂CH₂—(CH₂CH₂O)ₙ—R₁, wherein R₁ is H or a linear or branched lower alkyl group having from one to about 6 carbons, and n is a positive integer from about 3 to about 100; or a poly(ethylene glycol) chain-containing tether having the general formula —CH₂—(CH₂CH₂O)ₙ—(CH₂)ₘ-Z, in which n is a positive integer from about 3 to about 100, m is 2, 3, or 4, and Z is lipoic acid, wherein lipoic acid is covalently joined to the distal terminus of said poly(ethylene glycol) chain-containing tether.

16. A method for preparing a therapeutic 5-aminosalicylic acid derivative composition having the general formula:

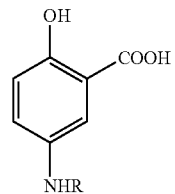

wherein R is a poly(ethylene glycol) chain-containing residue having the general formula —CH₂CH₂CH₂—(CH₂CH₂O)ₙ—R₁ R₁ is H or a linear or branched lower alkyl group having from one to about 6 carbons, and n is a positive integer from about 3 to about 100, comprising reacting the aldehyde group of a poly(ethylene glycol) chain-containing aldehyde with the amino group of 5-aminosalicylic acid to provide an imine intermediate and reducing the imine intermediate.

* * * * *